(12) United States Patent
Patel et al.

(10) Patent No.: US 8,691,197 B2
(45) Date of Patent: *Apr. 8, 2014

(54) IN-SHOWER LOTION COMPOSITIONS COMPRISING UP TO 10% FREE FATTY ACIDS WHEREIN RATIO OF UNSATURATED TO SATURATED FATTY ACIDS IS AT LEAST 1:1

(75) Inventors: Rajesh Patel, Middlebury, CT (US); Rosa Mercedes Paredes, Shelton, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 992 days.

This patent is subject to a terminal disclaimer.

(21) Appl. No.: 11/850,144

(22) Filed: Sep. 5, 2007

(65) Prior Publication Data
US 2009/0062390 A1    Mar. 5, 2009

(51) Int. Cl.
*A61K 8/00* (2006.01)
*A01N 37/00* (2006.01)
*A61K 31/20* (2006.01)

(52) U.S. Cl.
USPC ............................ 424/70.1; 514/557; 514/558

(58) Field of Classification Search
USPC ................................ 424/70.22; 514/557, 558
See application file for complete search history.

(56) References Cited

U.S. PATENT DOCUMENTS

| | | | |
|---|---|---|---|
| 4,661,343 A * | 4/1987 | Zabotto et al. ................... 424/59 |
| 5,175,190 A * | 12/1992 | Burton et al. .................. 514/560 |
| 5,427,704 A | 6/1995 | Lawate | |
| 5,445,822 A * | 8/1995 | Bracco ........................... 424/401 |
| 5,472,728 A | 12/1995 | Miller et al. | |
| 5,476,649 A * | 12/1995 | Naito et al. ................... 424/70.1 |
| 5,490,995 A | 2/1996 | Corrigan | |
| 5,578,299 A * | 11/1996 | Starch ......................... 424/78.03 |
| 5,631,012 A * | 5/1997 | Shanni ........................... 424/401 |
| 5,888,492 A | 3/1999 | Starch | |
| 5,928,632 A | 7/1999 | Reusch | |
| 5,965,500 A * | 10/1999 | Puvvada ........................ 510/130 |
| 5,976,516 A * | 11/1999 | Sakai et al. .................... 424/70.1 |
| 5,997,889 A * | 12/1999 | Durr et al. ....................... 424/401 |
| 6,156,369 A | 12/2000 | Eger et al. | |
| 6,323,246 B1 * | 11/2001 | Nakama et al. .................. 516/27 |
| 6,465,402 B1 * | 10/2002 | Lorant ........................... 510/136 |
| 6,645,511 B2 | 11/2003 | Aronson et al. | |
| 6,699,488 B2 | 3/2004 | Deckner et al. | |
| 6,716,440 B2 | 4/2004 | Aronson et al. | |
| 6,780,826 B2 | 8/2004 | Zhang et al. | |
| 6,903,057 B1 | 6/2005 | Tsaur | |
| 6,998,382 B2 | 2/2006 | Yang et al. | |
| 2003/0003066 A1 * | 1/2003 | Nichols et al. .................. 424/64 |
| 2004/0175350 A1 * | 9/2004 | Urgell Beltran et al. .. 424/70.27 |
| 2004/0223992 A1 | 11/2004 | Clapp et al. | |
| 2005/0227880 A1 * | 10/2005 | Shiloach et al. .............. 510/130 |
| 2005/0233015 A1 * | 10/2005 | Norberg et al. ................ 424/769 |
| 2007/0032393 A1 | 2/2007 | Patel et al. | |
| 2011/0250293 A1 * | 10/2011 | Blomberg ...................... 424/642 |

FOREIGN PATENT DOCUMENTS

EP        398 409        11/1990

OTHER PUBLICATIONS

Co-pending application: U.S. Appl. No. 11/748,943, filed May 15, 2007 to Patel et al.

* cited by examiner

*Primary Examiner* — Blessing M Fubara
*Assistant Examiner* — Jennifer A Berrios
(74) *Attorney, Agent, or Firm* — Ronald A. Koatz

(57) ABSTRACT

This invention relates to rinse-off skin conditioning compositions comprising relatively low amounts of oil/emollient and relatively low amounts of aqueous phase stabilizer/structurant. Use of unsaturated fatty acid (or at least minimum amount of unsaturated fatty acid as percentage of total fatty acid) has been found to result in unexpectedly high hydration. In a second embodiment, use of branched fatty acid (at minimum amount branched as percentage of total) also results in superior hydration. Also mixtures of unsaturated and branched fatty acids can be used.

In a second embodiment, the invention relates to method of enhancing hydration using compositions as noted.

3 Claims, 1 Drawing Sheet

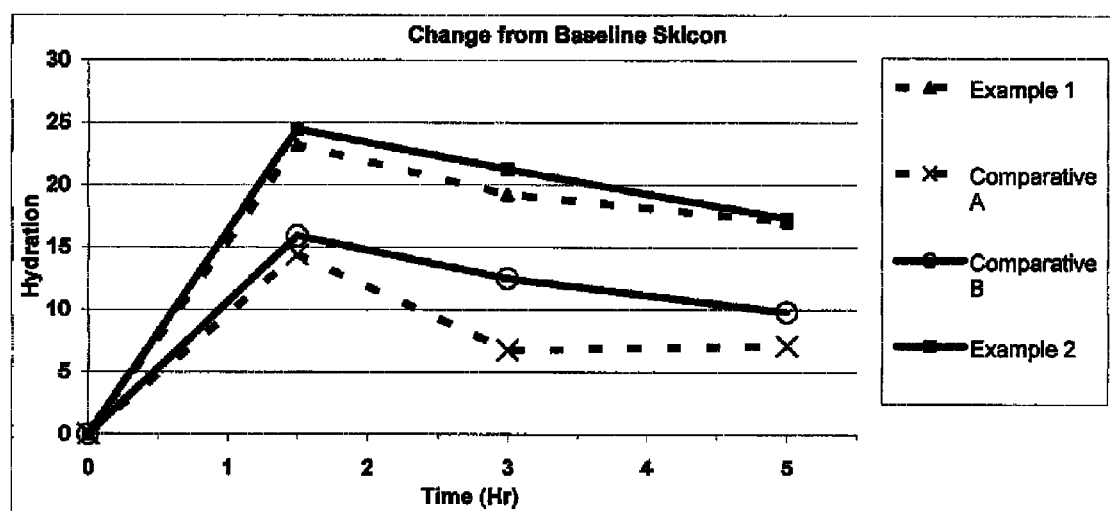

IN-SHOWER LOTION COMPOSITIONS COMPRISING UP TO 10% FREE FATTY ACIDS WHEREIN RATIO OF UNSATURATED TO SATURATED FATTY ACIDS IS AT LEAST 1:1

FIELD OF THE INVENTION

The present invention relates to wet skin treatment composition (in-shower lotions) designed for use during bathing to impart desirable properties to skin. Typically such compositions have little or no surfactant, are applied in the shower after cleansing and are rinsed off to achieve oil or emollient deposition while avoiding oily or greasy skin feel. The compositions are relatively low oil (typically having 20% or less oil), low structured (3% or less, preferably 2% or less) compositions.

BACKGROUND

Rinse-off conditions are known generally in the art. U.S. Pat. Nos. 5,578,299 and 5,888,492 both to Starch, for example describe rinse off conditioning compositions. Both references disclose the possible use of fatty acids as emollient, but fail to disclose use of unsaturated fatty acids or recognize the unexpected benefits unsaturated acids could bring. Emollients/oils also may comprise up to 40% of the compositions compared to generally lower oil compositions of the invention. In addition, both references require use of at least 1% nonionic surfactants. In preferred embodiments of the subject invention, the compositions comprise less than 1% by wt., preferably 0.5% or less, more preferably 0.15% or less surfactant and may preferably be absent altogether.

U.S. Pat. No. 5,928,632 to Reusch discloses rinse off skin conditioners which are surfactant free. There is no discussion of fatty acid and the only reference to fatty acid seems to be use of 0.5% stearic (saturated fatty acid) in a comparative formulation in Table 1.

U.S. Pat. No. 6,699,488 to Deckner discloses skin conditioning compositions comprising high internal phase (HIP) emulsion comprising oil, stabilizers and water. To the extent the compositions may contain fatty acids (column 9, lines 33-38), the reference teaches away from unsaturates and discloses the fatty acids are saturated (straight or branched chain).

U.S. Publication 2004/0223992 discloses wet skin compositions comprising gel networks which in turn comprise non-ionic hydrophilic surfactant and hydrophobic structuring agent (¶0040). The structuring agent may be saturated hydroxy fatty acid.

U.S. Pat. Nos. 6,645,511 or 6,716,440, both to Aronson et al. disclose wet skin compositions with non-greasy feel. The only mention of fatty acids seem to be as sensory modifiers (column 9, line 24 of '440), but there is no disclosure of use of unsaturated fatty acids or of ratio of unsaturates to saturates.

U.S. Pat. No. 6,903,057 to Tsaur discloses compositions comprising non-gelatinized starch structuring system which compositions may comprise fatty acid (e.g., skin benefit agent). The compositions must comprise surfactant and, in addition, there is no disclosure of unsaturated fatty acid or ratio of unsaturated to saturated. Applicants have filed a related application, (U.S. Publication No. 2007/0032393 A1) which is a wet skin composition having little or no surfactant. The reference discloses use of unsaturated fatty acid, but in a system where all examples have at least 4% structurant (i.e., non-pregelatinized starch structurant). Compositions of the invention comprise 3% or less structurant and no non-pregelatinized starch structurant. Compositions of the reference also must comprise 15% and up oil).

In applicants co-pending application Ser. No. 11/748,943. filed May 15, 2007, applicants disclose a relatively low oil shower gel with lower amounts of structurants. In this reference, although use of fatty acid is broadly disclosed, there is no recognition of criticality of unsaturated fatty acid (ratio of unsaturated to saturated of preferably at lest 1:1, more preferably 2:1) in a relatively low surfactant, low structurant system.

BRIEF DESCRIPTION OF THE INVENTION

Unexpectedly, applicants have now discovered that, in an oil in water emulsion system containing relatively low oil (20% or less, preferably 14% or less emollient), low structurant (3% or less, preferably 2% or less), low surfactant (2% or less, preferably 1% or less or absent altogether), in-shower lotion/gel systems, use of unsaturated fatty acid (e.g., oleic acid), relative to use of saturated fatty acid (in ratio of 1:1 or higher) unexpectedly enhances hydration when used in same system. Applicants have further discovered that use of branched fatty acid (i.e., isostearic acid) relative to use of un-branched (in ratio of 1:1 or higher) similarly enhances hydration More specifically, in one embodiment, the invention comprises shower agent composition comprising:
(1) 1 to 20%, preferably 1 to 14% hydrophobic phase (wherein the hydrophobic component(s) comprising the hydrophobic phase may be optionally thickened or structured);
(2) an aqueous phase comprising:
   (a) 50% by wt. or more water;
   (b) 5 to 25% hydrophilic benefit agent (e.g., humectants);
   (c) 0.1 to 3%, preferably 0.1 to 2% of aqueous phase structurant/stabilizer;
   (d) minors,
   wherein said compositions has 2% or less, preferably 1% or less surfactant;
   wherein said composition comprises 2 to 10% by wt., preferably 2.5 to 8% by wt. fatty acid and wherein the ratio of unsaturated to saturated fatty acid is at least 1:1, preferably at least 2:1 or greater and wherein, most preferably there is present at least 2.5% by wt. unsaturated fatty acid.

In a second embodiment, the invention comprises exactly the same composition noted above wherein ratio of branched to un-branched fatty acid is at least 1:1, preferably 2:1 or greater and wherein, most preferably, there is at least 2.5% branched fatty acid.

The unsaturated and branched fatty acid may be used together as long as the combination of unsaturated and/or branched fatty acid is at ratio of at least 1:1 relative to saturated, un-branched fatty acid.

In a third embodiment of the invention, the invention comprises a method of enhancing skin hydration (measured, for example, using Skicon Corneometer) which method comprises applying to the skin any of the compositions defined above.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

BRIEF DESCRIPTION OF THE FIGURES

FIG. 1 is a graph showing change in hydration (measured by change in Baseline Skicon data) which comprises identical shower lotion compositions comprising relatively low levels of oil/emollient (20% or under) and relatively low levels of polymer/structurant (preferably 2% or less). Thus, for example Example 1 and comparative B and Example 2 and Comparative A are each identical to one another except that the Examples comprise 3% unsaturated fatty acid (oleic) and the comparatives comprise 3% saturated fatty acid (lauric). From FIG. 1, it can be seen that use of unsaturated fatty acid results in much greater hydration.

DETAILED DESCRIPTION OF THE INVENTION

The present invention relates to liquid compositions commonly used in the shower having little or no surfactant and often referred to as shower gel compositions or in-shower lotions. They are often applied after cleansing during rinse, and are used to achieve deposition of oil or emollient. As such, they are also sometimes referred to as rinse-off conditioners.

Typically such lotions have used either low levels of surfactants (to act as emulsifiers for hydrophobic emollient phase) and/or relatively high levels of hydrophilic emollient. In a recently filed co-pending application, U.S. Ser. No. 11/748,943, filed May 15, 2007, applicants disclosed compositions with substantially no surfactant emulsifier, yet which maintain stable (no phase separation of emollient after 3 months at 40° C.). Stability is maintained using aqueous phase stabilizer which allowed the use of surprisingly less oil.

In the disclosure, although it is noted broadly that fatty acids can be used, nothing is said about using unsaturated and/or branched versus branched, saturated fatty acids. Surprisingly and unpredictably, applicants have found that when ratio of unsaturated to saturated fatty acid; or branched to un-branched fatty acid; or unsaturated and/or branched to saturated, branched fatty acid is at least 1:1; and/or when at least 2.5% by wt. unsaturated fatty and/or branched acid is used in absolute amount, there is a strong advantage in skin hydration relative to when branched, saturated fatty acids are used in predominance or solely.

The composition is described in greater detail below.
Hydrophobic Phase
Emollient/Oil The hydrophobic emollients of the invention are typically skin compatible oils by which is meant oils that are liquid at temperature at which bathing is carried out, and which are safe for use in cosmetics because they are inert to the skin or actually beneficial. Examples of such skin compatible oils include ester oils, hydrocarbon oils and silicone oils.

Ester oils as the name implies have at least one ester group in the molecule. One type of common ester oil useful in the present invention are the fatty acid mono and polyesters such as cetyl octanoate, octyl isonanoanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

A second type of useful esters oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives, provided they are liquids. Proprietary ester blends such as those sold by Finetex as Finsolv® are also suitable, as is ethylhexanoic acid glyceride.

A third type of ester oil is liquid polyester formed from the reaction of a dicarboxylic acid and a diol. An example of polyesters suitable for the present invention is the polyesters marketed by ExxonMobil under the trade name PURESYN ESTER®.

A second class of skin compatible oils suitable for the present invention is liquid hydrocarbons. These include linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Light (low viscosity) highly branched hydrocarbon oils are also suitable.

Petrolatum is a unique hydrocarbon material and a useful component of the present invention. Since it is only partially comprised of a liquid fraction at room temperature, it may be regarded as "structured oil phase" when present by itself or alternatively as a "structurant" when admixed with other skin compatible oils.

A third class of useful skin compatible oils is silicone based. They include linear and cyclic polydimethyl siloxane, organo functional silicones (alkyl and alkyl aryl), and amino silicones. Silicones may include pre-made emulsions such as Silicone 1788® from Dow Chemical.

In one embodiment of the invention, the emollient or oil may be structured to create a structured oil phase. As indicated above, petrolatum may itself be considered a "Structured Phase".

The structurant may, for example, be either an organic or inorganic structurant. Preferred inorganic structurants are hydrophobically modified silica or hydrophobically modified clay with particle size less than 1 micrometer. Examples are Bentone 27V, Bentone 38V or Bentone gel MIO V from Rheox, and Cab-O-Sil TS720 or Cab-O-Sil M5 from Cabot Corporation.

The organic structurants are either crystalline solids or amorphous gels with molecular weight less than 5,000 Daltons, preferably less than 3,000 Daltons.

Preferred organic structurants have a melting point greater than 35° C., preferably greater than 40° C. Especially preferred structurants are those that can form a solution with the selected skin compatible oil at a temperature higher than their melting point to form a free flowing clear solution. Upon cooling to the ambient temperature, the organic structurant precipitate from the oil phase to form a 3-dimensional crystal structure providing the physical properties set forth above.

Examples of organic thickeners suitable for the invention are solid fatty acid esters, natural or modified fats, fatty acid, fatty amine, fatty alcohol, natural and synthetic waxes, and petrolatum. Petrolatum is a preferred organic structuring agents.

Particularly preferred organic structurants are solid fatty acid esters and petrolatum. Examples of solid fatty esters are mono, di or tri glycerides derivatives of palmitic acid, stearic acid, or hydroxystearic acid; sugar fatty ester or fatty esters of dextrin. Examples of these polyol fatty acid esters are described in U.S. Pat. Nos. 5,427,704, 5,472,728, 6,156,369, 5,490,995 and EP Patent 398 409 incorporated by reference herein. Trihydroxystearin sold under the trade name of THIX-CIN® from Rheox Corporation is found particularly useful for structuring triglyceride ester oils.

The level of structurant present in a structured oil phase can be in the range of 1 to 90% and depends on the type of structurant used and the nature of the skin compatible oil. For solid organic structurants such as trihydroxystearin, the preferred level is 3 to 15%. Preferably, the exact levels used should provide a stable network having the desired viscosity in the range of 100 to 5000 poise measured at a shear rate of 1 Sec-1 and can be readily optimized by one skilled in the art.

The hydrophobic emollient (e.g., oil phase), as noted above, need not be structured or thickened. This is simply one embodiment since un-thickened oils may also be used. It is surprising that un-thickened oil stays stabilized simply because of stabilizer in aqueous phase.

The emollient oil found in and/or comprising the hydrophobic phase of the invention comprises 1 to 14%, preferably 1 to 13%, more preferably 2 to 12%, more preferably 3 to 11% by wt. of the total liquid composition of the invention.

As discussed above, the hydrophobic phase must also comprise 2 to 10% by wt., preferably 2.5 to 8% by wt. fatty acids, e.g., saturated and unsaturated $C_{14}$ to $C_{24}$ fatty acid. In one embodiment of the invention, the ratio of unsaturated to saturated fatty acid is at least 1:1, preferably at least 2:1. Preferably there is present at least 2.5% by wt. unsaturated fatty acid in an absolute amount and, typically, the composition may comprise entirely unsaturated fatty acid. The unsaturated fatty acid may also be combined with saturated fatty acid (branched and/or unbranched) as long as minimum ratios noted are maintained. Preferred unsaturated fatty acids include oleic acid.

In a second embodiment of the invention, the fatty acids are mixture of branched and un-branched fatty acids where ratio of branched to un-branched is at least 1:1, preferably at least 2:1. Preferably there is present at least 2.5% by wt. branched fatty acid in an absolute amount and the composition may comprise all branched fatty acid. A preferred fatty acid includes isostearic acid.

The unsaturated and branched fatty acids may also be used together as long as ratio of the combined unsaturated and/or branched fatty acid to saturated, un-branched fatty acid is again at least 1:1.

Unexpectedly, applicants have found that use of the fatty acid types and amounts noted in relatively low oil, low stabilizer compositions provides superior hydration.

Aqueous Phase

Compositions of the invention also comprise an aqueous phase as noted below.

The aqueous phase typically comprise at least 45%, preferably greater than 50%, more preferably greater than 55% by wt. water.

The aqueous phase further comprises 0% to 25%, preferably 5 to 25%, preferably 7 to 20% by wt. of a hydrophilic moisturizer or skin benefit agent. Examples of such compounds are polyols such as linear and breached chain alkyl polyhydroxyl compounds. These include, for example, propylene glycol, sorbitol and glycerin.

Also polymeric polyols are useful, such as polypropylene glycol, polyethylene glycol, butylene glycol and so forth.

The aqueous phase further must comprise 0.1 to 3%, preferably 0.1 to 2.0% by wt. of a stabilizer.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provides physical stability of the oil droplets, in the surfactant composition at 37° C., 40° C. or preferably 50° C. for at least 3 months.

Inorganic dispersion stabilizers suitable for the invention includes, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizer are defined here as organic molecules that have a molecular weight generally lower than 1000 Daltons and form a network in the aqueous phase that immobilizes the dispersed oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carton atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizers is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum.

An especially preferred types of polymeric dispersion stabilizer agent include acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

The compositions also comprise other ingredients typically founding liquid formulations.

Among these are included (without limitation) auxiliary thickeners (e.g., carboxymethyl cellulose, hydroxyethylcellulose); perfumes; sequestering agents (e.g., ethyl diamine tetra acetate, known as EDTA); cooling agents; opacifiers and pearlizers (e.g., zinc or magnesium stearate, titanium dioxide).

Other optionals include antimicrobial agents; preservatives (e.g., parabens, sorbic acid); suds boosters (e.g., coconut acyl mono- or diethanolamide); antioxidants; cationic conditioners (e.g., Merquat® and Jaguar® type conditioners), exfoliates; ionizing salts; organic acids (e.g., citric or lactic acid).

In a third embodiment, the invention relates to a method of enhancing hydration using amounts and types of fatty acid noted relative to compositions outside the defined ratios and amounts.

Protocol for Skicon Moisturization Measurements

Hydration measurements of the skin are made using Skicon 200® apparatus, which measures moisture content in the skin through conductance. Conductance measurements are made at baseline value, after the skin has been patted dry (optionally the skin can be pre-washed before drying). Hydration values are then based on conductance values based on change over baseline over time. The specific measurement using Skicon is described in "Evaluation of the Skin Surface Hydration in Vivo by Electrical Measurement" to Tagami et al., Journal of Investigative Dermatology (1980), 75, 500-507, which article is hereby incorporated by reference into the subject application.

Specific Measurement Protocol is as follows:
(1) Take baseline measurement of area to be measured (typically, the legs) after patting dry using Skicon 200®;
(2) Apply formulation tested (0.2 ml of test product) to a 6×6 cm area marked on tested leg or legs;
(3) Wash each site with product for 10 seconds;
(4) Lather remains on the skin for 90 seconds and is then rinsed off for 15 seconds;
(5) Post-application measurements are taken at 1.5 hours, 3 hours and 5 hours, for a total of 4 measurements;
(6) Comparisons between products are made using paired t-tests at each time point. Also, area under the curve analysis was employed as a measure of overall moisturization effect. Significance was determined with the p-value set at 0.05 for both methods.

EXAMPLES

Example 1, 2 and Comparative A & B

The following Table 1 sets forth Examples 1, 2 and Comparative A & B.

TABLE 1

|  | Ingredient | Example 1 | Example 2 | Comparative A | Comparative B |
| --- | --- | --- | --- | --- | --- |
| Oil | Soybean oil | 1.50% | 1.40% | 1.40% | 1.50% |
|  | Petrolatum | 7.50% | 12.50% | 12.50% | 7.50% |
|  | Mineral oil | 5.00% |  |  | 5.00% |
|  | Triglycerides |  | 1.40% | 1.40% |  |
|  | Miscellaneous oils |  | 0.90% | 0.90% |  |
| Polymer/ Structurant | Carbobol (Ultrez 21) | 0.15% | 0.15% | 0.15% | 0.15% |
|  | Pemulen TR2 | 0.35% | 0.35% | 0.35% | 0.35% |
|  | Xanthan Gum | 0.20% | 0.20% | 0.20% | 0.20% |
| Humectant | Glycerin | 19.20% | 19.20% | 19.20% | 19.20% |
| Fatty Acid | Oleic acid (unsaturated) | 3.00% | 3.00% |  |  |
|  | Lauric acid (saturated) |  |  | 3.00% | 3.00% |
| pH Adjust | Sodium Hydroxide | 0.05% | 0.05% | 0.05% | 0.05% |
| Preservatives & Fragrance | Decyl Glucoside (as 100%) | 1.75% | 1.75% | 1.75% | 1.75% |
|  | EHDP | 0.05% | 0.05% | 0.05% | 0.05% |
|  | Tetrasodium EDTA | 0.02% | 0.02% | 0.02% | 0.02% |
|  | DMDM Hydantoin/ Iodopropylbutylcarbamate | 0.10% | 0.10% | 0.10% | 0.10% |
|  | Fragrance |  | 0.50% | 0.50% |  |
|  | Water | 57.97% | 55.77% | 55.77% | 57.97% |
| Area Under Curve |  | 5130.7 | 5475.36 | 3335 | 2435.71 |
|  |  | 0.15 | 0.64 | 0.04 | 0 |

Example 1 is identical to Comparative B and Example 2 is identical to Comparative A except that, in Examples 1 and 2, unsaturated oleic is used and, in the comparatives, saturated lauric acid is used. As seen in FIG. 1, use of unsaturated fatty acid results in far greater hydration. This can also be seen in Table 1 where "Area Under Curve" value is measured.

Examples 3 & 4

The following Table 2 sets forth Example 3 and Comparative C

TABLE 2

| Function | Ingredient | Example 3 | Comparative C |
|---|---|---|---|
| Oil | Petrolatum | 10.5% | 10.5% |
| | Octyldodecanol | 0.315% | 0.315% |
| | Polydecene | 0.315% | 0.315% |
| | Soybean | 3.5% | 3.5% |
| Polymer/Structurant | Carbopol | 0.137% | 0.137% |
| | Pemulen TR2 | 0.239% | 0.239% |
| | Xanthan gum | 0.137% | 0.137% |
| Humectant | Glycerin | 10.0% | 10.0% |
| Fatty Acid | Lauric acid | 1.05% | 2.10% |
| | Isostearic acid | 1.05% | |
| pH Adjust | Sodium hydroxide | q.s to pH 6.0 | q.s to pH 6.0 |
| Emulsifier/non-ionic surfactant | Decyl glucoside | 1.9% | 1.9% |
| Preservative | Phenoxyethanol | 0.4% | 0.4% |
| | Paraben | 0.3% | 0.3% |
| | Fragrance | 0.7% | 0.7% |
| | TiO$_2$ | 0.15% | 0.15% |
| Area under curve | | 38.65 | 16.7 |

Example 3 is identical to Comparative C except Example C used branched to un-branched fatty acid in ratio if at least 1:1. As seen in Table 2, use of branched fatty acid results in greater hydration. This is also seen from an "Area Under Curve" value which more than 2 times as great at 38.65 for Example 3 versus 16.7 for Comparative C. Area under curve is measured of overall moisturization.

The invention claimed is:

1. Liquid composition consisting of:
   (1) 1 to 20% by wt. of a hydrophobic phase which consists of:
      a) an oil selected from the group consisting of ester oils, hydrocarbon oils, petrolatum, silicone oil and mixtures thereof; and
      b) about 3% by wt. of the total composition of oleic acid; and
   (2) an aqueous phase consisting of:
      a) 50% or more by wt. water;
      b) 5 to 25% hydrophilic benefit agent;
      c) 0.1 to 3% aqueous phase stabilizer; and
      d) optional ingredients selected from the group consisting of auxiliary thickeners, perfumes, sequestering agents, cooling agents, opacifiers and pearlizers, antimicrobial agents, preservatives, suds boosters, antioxidants, cationic conditioners, exfoliants, ionizing salts, organic acids and mixtures thereof;
   wherein the composition has 2% or less surfactant;
   and wherein said composition is an in-shower, rinse off composition for achieving oil or emollient deposition while avoiding oily or greasy skin feel.

2. The composition according to claim 1, wherein the aqueous phase stabilizer in the aqueous phase is at 0.1 to 2%.

3. A method of enhancing skin hydration which method comprises applying to the skin a composition of claim 1.

* * * * *